United States Patent [19] [11] 4,404,410
Cornils et al. [45] Sep. 13, 1983

[54] PROCESS FOR PREPARING 2,3-DIMETHYL-2,3-BUTANEDIOL

[75] Inventors: Boy Cornils, Dinslaken; Jürgen Weber, Oberhausen; Wolfgang Bernhagen, Mülheim; Helmut Springer, Oberhausen, all of Fed. Rep. of Germany

[73] Assignee: Ruhrchemie Aktiengesellschaft, Oberhausen, Fed. Rep. of Germany

[21] Appl. No.: 272,229

[22] Filed: Jun. 10, 1981

Related U.S. Application Data

[63] Continuation of Ser. No. 83,894, Oct. 11, 1979, abandoned.

[30] Foreign Application Priority Data

Oct. 13, 1978 [DE] Fed. Rep. of Germany ....... 2844637

[51] Int. Cl.³ ............................................. C07C 31/20
[52] U.S. Cl. .................................................... 568/858

[58] Field of Search ................................ 568/860, 858

[56] References Cited

U.S. PATENT DOCUMENTS 2,437,648  3/1948  Milas ................................. 568/860
2,492,201  12/1949  Swern et al. ....................... 568/860
2,739,173  3/1956  Corey et al. ........................ 568/860

*Primary Examiner*—J. E. Evans
*Attorney, Agent, or Firm*—Sprung, Horn, Kramer & Woods

[57] ABSTRACT

An improved process for the preparation of 2,3-dimethyl-2,3-butanediol is disclosed wherein hydrogen peroxide and 2,3-dimethylbutene are reacted with formic acid at 50° to 70° C. while stirring, the 2,3-dimethylbutene and hydrogen peroxide being introduced into the formic acid simultaneously but separately. The diol can be obtained by hydrolysis of the pinacol monoformate formed.

8 Claims, No Drawings

PROCESS FOR PREPARING 2,3-DIMETHYL-2,3-BUTANEDIOL

This is a continuation of application Ser. No. 083,894, filed Oct. 11, 1979, now abandoned.

BACKGROUND OF THE INVENTION

1. Field of the Invention

The present invention relates to a process for preparing 2,3-dimethyl-2,3-butanediol (pinacol).

2. Discussion of Prior Art

It is known to prepare diols by hydroxylating olefins with hydrogen peroxide in the presence of metal oxides as catalysts. According to another variant of this reaction, the unsaturated compounds are reacted with hydrogen peroxide in the presence of acids, preferably carboxylic acids. In this case the percarboxylic acid formed under the reaction conditions acts as a hydroxylating agent. In the hydroxylation, esters are first of all formed, which are then hydrolyzed to the corresponding diol in a second reaction step.

Normally the corresponding percarboxylic acid is prepared from hydrogen peroxide and acid in a separate reaction before the actual hydroxylation, and is then reacted with the olefin.

Processes that avoid the separate preparation of the peracid and use instead a mixture of hydrogen peroxide and carboxylic acid from which the relevant peracid is formed, are simpler.

The afore-mentioned processes have the disadvantage that they always involve the formation of free peracids in a fairly high concentration. Since peroxides and olefins lead to formation of explosive mixtures, these processes have proven unsuitable on safety grounds for use on a commercial scale. Moreover, the high peracid concentration reduces the yield of end product since the glycol initially obtained reacts further with excess peracid to produce undesired by-products.

The problem therefore arose of providing a process which prepares 2,3-dimethyl-2,3-butanediol in a simple and safe manner, and which ensures that the diol is obtained in high yields.

SUMMARY OF INVENTION

According to the invention, this objective is achieved by reacting 2,3-dimethylbutene with hydrogen peroxide, in the preparation of 2,3-dimethyl-2,3-butanediol, in such a way that 2,3-dimethylbutene-2 and hydrogen peroxide are introduced simultaneously but separately into formic acid at 50° to 70° C. and while stirring.

It has surprisingly been found that pure 2,3-dimethylbutene-2 and also mixtures of 2,3-dimethylbutene-2 and 2,3-dimethylbutene-1 with a proportion of up to about 30% by weight (relative to the total mixture) of 2,3-dimethylbutene-1 can be used without reaction products other than the desired 2,3-dimethyl-2,3-butanediol being formed. This behavior of the olefin mixture was unexpected, since 2,3-dimethylbutene-1 in the normal course of the reaction would have been preferentially converted into 2,3-dimethyl-1,2-butanediol. Of course, it is known that the hydroxylation reaction with hydrogen peroxide in the presence of carboxylic acids can also lead to rearrangements. However, only a certain proportion of the olefin used and not the whole amount is rearranged, with the result that a uniform reaction product is formed.

2,3-dimethylbutene-1 and 2,3-dimethylbutene-2 are easily accessible starting materials. They are obtained for example by dimerizing propylene and are then in sufficient purity to be used either after prior distillation or directly in the process according to the invention.

Mixtures of 2,3-dimethylbutene-1 and 2,3-dimethylbutene-2 can also be obtained by dehydrating 2,3-dimethylbutanol-1 in the presence of conventional dehydrating catalysts such as aluminum oxide. They too can be used in the process according to the invention without prior purification.

An essential feature of the new process is the separate addition of the reactants, namely olefin and hydrogen peroxide, to the formic acid. The reaction is carried out on a commercial scale by heating the formic acid to the reaction temperature, i.e. to 50° to 70° C., and then adding olefin and hydrogen peroxide in an amount such that the liberated heat of reaction is sufficient to maintain the reaction temperature. The hydrogen peroxide is used in the form of a 30 to 50% aqueous solution.

The formic acid exists in the pure form or as a mixture containing up to 20% by weight of water. At least two moles of formic acid are used per mole of olefin. Excess formic acid does not interfere with the reaction. The molar ratio of olefin to hydrogen peroxide is 1:1, but broadly can be 0.2 to 2.0:1.

In order to ensure an intimate mixing of olefin and hydrogen peroxide, it is essential to stir the reaction mixture intensively such as by rotating a stirrer. Under laboratory conditions for example a stirrer rotates at a velocity of at least 500 rpm.

Under the reaction conditions and the special manner in which the reaction is carried out, the olefin reacts spontaneously to form pinacol monoformate. After the end of the addition of olefin and hydrogen peroxide, the reaction mixture is left to react further for one hour at the reaction temperature, and the diol is liberated by hydrolyzing the reaction solution with an aqueous alkali hydroxide.

The organic phase is then separated and the aqueous phase is extracted with an organic solvent, e.g. isobutanol. The combined organic phases are worked up by fractional distillation to give pure 2,3-dimethyl-2,3-butanediol.

In the following two examples the superiority of the process according to the invention (embodiment example) is illustrated by comparison with a process according to the state of the art (comparison example).

The results achieved by the process according to the invention are evident from the embodiment example.

COMPARISON EXAMPLE 325 g of 85% formic acid and 293 g of 36% hydrogen peroxide are heated to 60° C. in a round-bottomed flask. 252 g of 2,3-dimethylbutene, consisting of 79% of 2,3-dimethyl-2-butene and 21% of 2,3-dimethyl-1-butene, are then pumped in over a period of one hour. The reaction that is thereby initiated requires a moderate degree of cooling. After a further two hours at 60° C. the reaction mixture is almost homogeneous. The reaction mixture is then worked up by neutralization with caustic soda, phase separation, and distillation. The crude product contains, in addition to 43% pinacol and 38% of unreacted starting olefin, approximately 10% of 2,3-dimethyl-1,2-butanediol. On account of the close boiling points of pinacol and 2,3-dimethyl-1,2-butanediol, distillative purification cannot be carried out in practice. After removing the unreacted olefin, which can be returned to the synthesis, a second fraction containing only 90% pinacol is obtained as head product.

EMBODIMENT EXAMPLE 325 g of 85% formic acid are heated to 60° C. in a round-bottomed flask and 293 g of 36% hydrogen peroxide and 252 g of 2,3-dimethylbutene (79% 2,3-dimethyl-2-butene, 21% of 2,3-dimethyl-1-butene) are added via two separate pumps while stirring and at such a rate that the internal temperature is maintained at 60° C. The reaction is complete two hours after the end of the addition. The fully homogeneous reaction mixture is now neutralized and freed from the aqueous phase. The crude product has the following composition, as shown by gas chromatography: 80% pinacol, 7% 2,3-dimethylbutene and 0.1% of isomeric diols; the remainder consists of acetone, pinacolone and an unidentified head component. The pinacol was identified by its boiling point of 105° C. at 50 mm Hg and its melting point of 42° to 43° C.

241 g of an anhydrous, 99.6% pinacol are obtained by fractional distillation in the presence of a suitable water entrainment agent.

A further generally applicable method for optimizing the yield is to extract the aqueous phase with a suitable organic solvent (e.g. isobutanol), combine the combined extracts with the organic phase containing the main amount of pinacol, and subject the whole to distillation. The solvent in this case simultaneously acts as an azeotrope-forming component for the recovery of anhydrous pinacol.

What is claimed is:

1. A process for preparing 2,3-dimethyl-2,3-butandiol which comprises introducing into a reaction vessel containing formic acid at 50° to 70° C. while stirred, 2,3-dimethylbutene and hydrogen peroxide, said 2,3-dimethylbutene and hydrogen peroxide being introduced into said formic acid simultaneously but separately and thereafter hydrolyzing pinacol monoformate so formed.

2. A process according to claim 1, wherein said 2,3-dimethylbutene comprises a mixture of 2,3-dimethylbutene-2 and up to 30% by weight of 2,3-dimethylbutene-1.

3. A process according to claim 1 wherein said 2,3-dimethylbutene is 2,3-dimethylbutene-2.

4. A process according to claim 1 wherein said hydrogen peroxide is employed in the form of a 30 to 50% aqueous solution.

5. A process according to claim 1 wherein said formic acid is employed in pure form or in the form of a mixture containing up to 20% by weight water.

6. A process according to claim 1 wherein the molar ratio of 2,3-dimethylbutene to hydrogen peroxide is 0.2–2.0:1.

7. A process according to claim 1 wherein said 2,3-dimethylbutene is 2,3-dimethylbutene-1.

8. A process according to claim 7, wherein said 2,3-dimethylbutene-1 is in admixture with 2,3-dimethylbutene-2.

* * * * *